United States Patent [19]

Bluthe et al.

[11] 4,421,934
[45] Dec. 20, 1983

[54] PROCESS FOR THE PREPARATION OF δ-ETHYLENIC CARBONYL COMPOUNDS

[75] Inventors: Norbert Bluthe; Jacques Gore, both of Calluire; Max Malacria, Villeurbanne, all of France

[73] Assignee: Rhone-Poulenc Sante, Courbevoie, France

[21] Appl. No.: 354,145

[22] Filed: Mar. 5, 1982

[30] Foreign Application Priority Data

Mar. 9, 1981 [FR] France .................................. 81 04600
Jun. 23, 1981 [FR] France .................................. 01 12300

[51] Int. Cl.³ .................................................. C07C 45/51
[52] U.S. Cl. ..................................... 568/341; 568/384
[58] Field of Search .................................. 568/341, 384

[56] References Cited

U.S. PATENT DOCUMENTS 4,222,963 9/1980 Fujita et al. ......................... 568/384

OTHER PUBLICATIONS

Miyashi et al., Chem. Abst., vol. 91, #19210u (1979).
Viola et al., J.A.C.S., vol. 89, p. 3462 (1907).
Fujita et al., Chem. Comm, p. 272 (1978).
Fujita et al., Synthesis, p. 934, (1978).
Roumestant et al., Tet, vol. 33, p. 1283 (1977).
Doutheau et al., Tet, vol. 36, p. 1953 (1980).

Evans et al., J.A.C.S., vol. 97, p. 4765 (1975).

*Primary Examiner*—James H. Reamer
*Attorney, Agent, or Firm*—Stevens, Davis, Miller & Mosher

[57] ABSTRACT

Process for the preparation of δ-ethylenic carbonyl compounds of the formula (I) by the oxy-Cope rearrangement of a diethylenic alcohol of the formula (II), in the presence of a mercuric salt: in formulae (I) and (II), $R_1$, $R_2$, $R_4$, $R_5$ and $R_6$, which are identical or different, represent a hydrogen atom or an acyclic hydrocarbon radical and $R_3$ represents an acyclic hydrocarbon radical, it being understood that $R_1$ and $R_3$ can together form a trimethylene radical, or alternatively that $R_3$ and $R_4$ can together form an alkylene radical containing 3 to 20 carbon atoms.

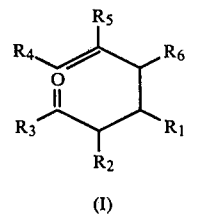 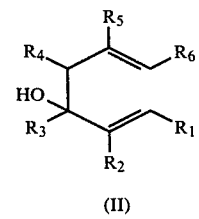

(I)            (II)

8 Claims, No Drawings

PROCESS FOR THE PREPARATION OF δ-ETHYLENIC CARBONYL COMPOUNDS

DESCRIPTION

The invention relates to a process for the preparation of δ-ethylenic carbonyl compounds useful as intermediates in the synthesis of products of use in pharmacy, agrochemistry or perfumery.

The invention provides a process for the preparation of δ-ethylenic carbonyl compounds of the general formula:

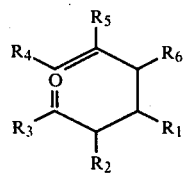

(I)

in which $R_1$, $R_2$, $R_4$, $R_5$ and $R_6$, which are identical or different, represent hydrogen or a hydrocarbon radical and $R_3$ represents a hydrocarbon radical, it being understood that $R_1$ and $R_3$ can together represent a trimethylene radical, or alternatively that $R_3$ and $R_4$ can together represent an alkylene radical $(-CH_2-)_n$, in which one or more carbon atoms may be substituted by one or more alkyl radicals containing 1 to 4 carbon atoms, and in which n represents an integer from 3 through 20 inclusive, by the rearrangement of a diethylenic alcohol of the general formula:

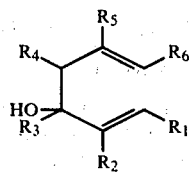

(II)

in which $R_1$, $R_2$, $R_3$, $R_4$, $R_5$ and $R_6$ are defined as above, using a mercuric salt as hereinafter described.

The term "hydrocarbon radical" is to be understood as meaning an acyclic radical containing 1 to 20 carbon atoms, the chain of which may contain one or more double or triple bonds.

The products of the general formula (I) are particularly valuable intermediates for the preparation of products having a biological activity. More precisely, the products of the general formula (I) are applied in the synthesis of products intended for pharmacy (vitamins A and E), agrochemistry or perfumery.

The rearrangement of a diethlenic alcohol of the general formula (II) to give a product of the general formula (I) is a known reaction which is generally referred to as the oxy-Cope rearrangement. The oxy-Cope rearrangement has been the subject of much work, but, in view of the conditions used for carrying it out, its practical value has been very limited.

For example, vapour-phase thermolysis, according to the process described by A. Viola et al., J. Amer. Chem. Soc., 89, 3462 (1967), is of low stereoselectivity and leads to by-products from degradation and polymerisation, the origin of which is due to the high temperatures (of the order of 300° C.) required for the rearrangement.

It has been shown, in particular by Y. Fujita et al., Chem. Comm., 272 (1978), and Synthesis, 934 (1978), by M. L. Roumestant et al., Tetrahedron, 33, 1283 (1977), and by A. Doutheau et al., Tetrahedron, 36, 1953 (1980), that the yield and the stereoselectivity are increased by carrying out the reaction in an aprotic polar solvent such as N-methylpyrrolidone or diglyme, under reflux. Furthermore, D. A. Evans and A. M. Golob, J. Amer. Chem. Soc., 97, 4765 (1975), have shown that the potassium alcoholates rearrange more easily than the alcohols themselves. Thus, some alcohols of the general formula (II), treated with potassium hydride in tetrahydrofuran under reflux, lead to the corresponding δ-ethylenic carbonyl products. However, these conditions are not suitable for the rearrangement of compounds having a low stability in a very basic medium.

It has now been found that the oxy-Cope rearrangement of a diethylenic alcohol of general formula II to a δ-ethylenic compound of general formula I can be carried out at a temperature from −40° C. to 80° C. and preferably from −5° C. to 30° C., either in the presence of a substantially stoichiometric amount of a mercuric salt, or in the presence of a catalytic amount of a mercuric salt and a substantially stoichiometric amount of a lithium salt; it is this finding which forms the subject of the present invention.

In order to obtain the best results in the absence of secondary reactions it is desirable to avoid the use of nucleophilic solvents, such as alcohols or water, or of precursors of nucleophilic anions, such as mercuric acetate.

If the rearrangement is carried out in the presence of a substantially stoichiometric amount of a mercuric salt, the reaction is advantageously performed in the presence of mercuric chloride or mercuric acetate which has been rendered sufficiently electrophilic by the use of a very polar solvent such as a mixture of tetrahydrofuran and water. However, the best results are obtained by using mercuric trifluoroacetate, which, whilst being more electro-philic than mercuric chloride or acetate, has the additional advantage of being soluble in a certain number of organic solvents such as methylene chloride.

The δ-ethylenic ketone of the general formula (I) is generally isolated after the reaction mixture has been treated with a reducing agent in a basic medium. It is preferred to use an alkali metal, e.g. sodium, borohydride in an aqueous solution of sodium hydroxide.

If the rearrangement is carried out in the presence of a catalytic amount of mercuric salt and a substantially stoichiometric amount of lithium salt, the reaction is advantageously performed in the presence of mercuric trifluoroacetate, which has the advantage of being soluble in organic solvents such as methylene chloride or benzene.

The catalytic amount of mercuric salt generally used is an amount of 0.01 to 0.3 mol per mol of diethylenic alcohol of the formula (II) used. A molar ratio of about 0.2 is particularly suitable and is preferred.

The preferred lithium salts which make it possible to obtain the best results are the trifluoroacetate and the trifluoromethanesulphonate. In general, the lithium salt is used in an amount of 1 mol per mol of diethylenic alcohol of the formula (II).

The reaction is generally complete after 1 to 30 hours at a temperature between −5° and 30° C.

When a catalytic amount of a mercuric salt is used the δ-ethylenic ketone of the general formula (I) is generally isolated after the reaction mixture has been treated with a basic aqueous solution such as a saturated solution of sodium bicarbonate.

If desired, the mercuric salt used as a catalyst can be regenerated and used to carry out a subsequent oxy-Cope rearrangement.

The δ-ethylenic ketone of the general formula (I) can also be isolated after the reaction mixture has been treated with a reducing agent in a basic medium, such as an alkali metal, e.g. sodium, borohydride in an aqueous solution of sodium hydroxide.

The δ-ethylenic ketone of the general formula (I) can be purified by applying physical methods such as distillation or chromatography.

The process of the invention is stereoselective when the symbol $R_4$ is other than hydrogen. The geometry of the ketone of general formula I obtained does not depend on the geometry of the starting alcohol of general formula II: when $R_4$ is other than hydrogen the stereochemistry of the double bond is controlled under the conditions indicated.

In the process of the invention the symbols $R_1$ to $R_6$ in the diethylenic alcohol of general formula II preferably have the following values: $R_2$ and $R_6$ represent a hydrogen atom, $R_1$ and $R_5$ represent a hydrogen atom or an alkyl radical containing 1 to 4 carbon atoms, $R_3$ represents an alkyl radical containing 1 to 4 carbon atoms and $R_4$ represents a hydrogen atom, an alkyl radical containing 1 to 4 carbon atoms or an alkenyl radical containing 2 to 5 carbon atoms, or alternatively $R_1$ and $R_3$ together represent a trimethylene radical, the symbols $R_2$, $R_4$, $R_5$ and $R_6$ being defined as above, or alternatively $R_3$ and $R_4$ together represent an alkylene radical —$(CH_2)_n$— in which n is from 3 through 12 inclusive, the symbols $R_1$, $R_2$, $R_5$ and $R_6$ being defined as above.

The following Examples illustrate the invention.

EXAMPLE 1

A mixture of 3,5-dimethylhexa-1,5-dien-3-ol (0.126 g, $10^{-3}$ mol) and mercuric chloride (0.270 g) in a mixture of tetrahydrofuran and water (1/1 by volume) (5 cc) is kept at a temperature of the order of 20° C. After a reaction time of 4 hours, the reaction mixture is filtered to remove the metallic mercury which has formed.

The reaction mixture is extracted with diethyl ether (3×25 cc). After drying over sodium sulphate and evaporation of the solvent under reduced pressure (20 mm Hg, 2.7 kPa), 6methylhept-6-en-2-one (0.040 g) is obtained, the characteristics of which are as follows: B.p. (101.3 kPa)=142°–144° C.; Infra-red spectrum of a liquid film: characteristic bands at 3070, 1720, 1650 and 890 cm$^{-1}$;

NMR spectrum (CDCl$_3$, δ in ppm, J in Hz): 1.65 (s, 3H); 1.7 to 2.0 (m, 4H); 2.10 (s, 3H); 2.30 (t, J=7, 3H); 4.65 (s broadened, 2H).

The characteristics of this product are in agreement with those which have been described by Viola et al., J. Amer. Chem. Soc., 89, 3462 (1967).

The yield is 32% relative to the alcohol used.

EXAMPLE 2

A mixture of 3,5-dimethylhexa-1,5-dien-3-ol (0.126 g, $10^{-3}$ mol) and mercuric trifluoroacetate (0.427 g) in a mixture of tetrahydrofuran and water (1/1 by volume) (5 cc) is kept at a temperature of the order of 20° C. After a reaction time of 10 minutes, the reaction mixture is filtered to remove the metallic mercury which has formed.

The reaction mixture is extracted with diethyl ether (3×25 cc). After drying over sodium sulphate and evaporation of the solvent under reduced pressure (20 mm Hg; 2.7 kPa), 6-methylhept-6-en-2-one (0.054 g), the characteristics of which are identical to those of the product obtained in Example 1, is obtained with a yield of 43%.

EXAMPLE 3

A mixture of 3,5-dimethylhexa-1,5-dien-3-ol (0.126 g, $10^{-3}$ mol) and mercuric trifluoroacetate (0.427 g) in methylene chloride (7.5 cc) is kept at a temperature of the order of 20° C. After a reaction time of 10 minutes, a solution of sodium borohydride (0.010 g) in 3 N sodium hydroxide solution (0.67 cc) is added to the reaction mixture. The reaction mixture is extracted with methylene chloride (3×25 cc). After drying over sodium sulphate and evaporation of the solvent under reduced pressure (20 mm Hg; 2.7 kPa), 6-methylhept-6-en-2-one (0.095 g), the characteristics of which are identical to those of the product of Example 1, is obtained with a yield of 75%.

EXAMPLE 4

By following the conditions of Example 3, but starting from 3,4-dimethylhexa-1,5-dien-3-ol (0.126 g, $10^{-3}$ mol) and mercuric trifluoroacetate (0.427 g) in methylene chloride (7.5 cc), oct-6-en-2-one (0.078 g) containing 80% of the E form is obtained, the characteristics of which are as follows: Infra-red spectrum of a liquid film: characteristic bands at 3020, 1720 and 970 cm$^{-1}$;

NMR spectrum (CDCl$_3$; δ in ppm; J in Hz): 1.65 (dd, 3H, J=5 and 2); 1.7 to 2.0 (m, 4H); 2.1 (s, 3H); 2.35 (t, 2H, J=7); 5.25–5.50 (m, 2H).

The yield is 62% relative to the alcohol used.

EXAMPLE 5

By following the conditions of Example 3, but starting from 3-hydroxy-3-(2-methylprop-2-enyl)-cyclohexene (0.152 g, $10^{-3}$ mol) and mercuric trifluoroacetate (0.427 g) in methylene chloride (7.5 cc), 3-(2-methylprop-2-enyl)-cyclohexan-1-one (0.023 g) is obtained, the characteristics of which are as follows: Infra-red spectrum of a liquid film: characteristic bands at 3080, 1720, 1690 and 895 cm$^{-1}$;

NMR spectrum (CDCl$_3$; δ in ppm, J in Hz): 1.7 (s, broad, 3H); 1.5–2.3 (broad signal, 11H); 4.8 (broad signal, 2H).

The yield is 15% relative to the alcohol used.

EXAMPLE 6

By following the conditions described in Example 3, but starting from 4,5-dimethylhepta-2,6-dien-4-ol (0.140 g, $10^{-3}$ mol) and mercuric trifluoroacetate (0.427 g) in methylene chloride (7.5 cc), 4-methyloct-6-en-2-one (0.070 g) containing 80% of the E form is obtained, the characteristics of wich are as follows: Infra-red spectrum of a liquid film: characteristic bands at 3015, 1720 and 975 cm$^{-1}$;

NMR spectrum (CDCl$_3$; δ in ppm; J in Hz): 0.97 (d, 3H, J=7); 1.65 (dd, 3H, J=5 and 2); 1.7–1.95 (m, 3H); 2.07 (s, 3H); 2.3 (broad signal, 2H); 5.2–5.5 (m, 2H).

The yield is 50% relative to the alcohol used.

EXAMPLE 7

A mixture of 4-isopropenyl-3,7-dimethylocta-1,6-dien-3-ol (0.195 g, $10^{-3}$ mol) and mercuric trifluoroacetate (0.475 g) in methylene chloride (10 cc) is kept at a temperature of the order of −5° C. The mixture is left to react for 10 minutes at this temperature, and the temperature is then allowed to rise to about 20° C. After 1 hour 30 minutes, a solution of sodium borohydride (0.010 g) in 0.3 N sodium hydroxide solution (7.3 cc) is added to the reaction mixture. The reaction mixture is extracted with methylene chloride (3×10 cc). The organic extracts are dried over magnesium sulphate. After filtration and concentration of the solvent under reduced pressure (20 mm Hg; 2.7 kPa), 6,10-dimethylundeca-6,9-dien-2-one (0.019 g) is obtained with a yield of 10% and has the following characteristics: Infra-red spectrum of a liquid film: characteristic band at 1720 cm$^{-1}$;

NMR spectrum (CDCl$_3$, δ in ppm, J in Hz): 1.5 to 1.8 (broad signal, 11H); 1.95 (t, 2H); 2.07 (s, 3H); 2.34 (t, J=7, 2H); 2.60 (dd, 2H); 4.8 to 5.3 (m, 2H).

EXAMPLE 8

A mixture of 2-isopropenyl-1-vinylcyclohexan-1-ol (0.166 g, 10$^{-3}$ mol) and mercuric trifluoroacetate (0.423 g) in methylene chloride (10 cc) is kept at a temperature of the order of 20° C. After a reaction time of 5 minutes, a solution of sodium borohydride (0.010 g) in 3 N sodium hydroxide solution (0.66 cc) is added to the reaction mixture. The reaction mixture is extracted with methylene chloride (3×10 cc). The organic extracts are dried over magnesium sulphate. After filtration and concentration of the solvent under reduced pressure (20 mm Hg; 2.7 kPa), 5-methylcyclodec-5-en-1-one (0.024 g) is obtained, the characteristics of which are as follows: Infra-red spectrum of a liquid film: characteristic bands at 2980 and 1710 cm$^{-1}$;

NMR spectrum (CDCl$_3$; δ in ppm, J in Hz): 1.47 (s, 3H); 1.55 to 2.15 (broad signal, 10H); 2.15 to 2.63 (broad signal, 4H); 5.2 (t, J=7, 1H).

EXAMPLE 9

A mixture of 1,2-divinylcyclododecan-1-ol (0.125 g, 5.10$^{-4}$ mol) and mercuric trifluoroacetate (0.215 g) in methylene chloride (4 cc) is kept at a temperature of the order of 20° C. After a reaction time of 1 hour 30 minutes, a solution of sodium borohydride (0.005 g) in 3 N sodium hydroxide solution (0.33 cc) is added to the reaction mixture. The reaction mixture is extracted with methylene chloride (3×10 cc). The organic extracts are dried over magnesium sulphate. After filtration and concentration of the solvent under reduced pressure (20 mm Hg; 2.7 kPa), cyclohexadec-5-en-1-one (0.087 g) is obtained with a yield of 70%.

EXAMPLE 10

A mixture of 3,5-dimethylhexa-1,5-dien-3-ol (0.630 g, 5.10$^{-3}$ mol), lithium trifluoroacetate (0.600 g, 5.10$^{-3}$ mol) and mercuric trifluoroacetate (0.427 g, 10$^{-3}$ mol) in freshly distilled methylene chloride (70 cc) is kept at a temperature of the order of 20° C., under an inert atmosphere. After a reaction time of 5 hours, the reaction mixture is washed with a saturated aqueous solution of sodium bicarbonate (3×25 cc). After the organic phase has been dried over magnesium sulphate, the solvent is evaporated off under reduced pressure (20 mm Hg; 2.7 kPa).

6-Methylhept-6-en-2-one (0.567 g), the characteristics of which are identical to those of the product obtained in Example 1, is thus obtained with a yield of 90%.

EXAMPLE 11

The conditions of Example 10 are followed, but the starting materials are 3,4-dimethylhexa-1,5-dien-3-ol (0.126 g, 10$^{-3}$ mol), lithium trifluoroacetate (0.120 g, 10$^{-3}$ mol) and mercuric trifluoroacetate (0.120 g, 0.28.10$^{-3}$ mol) in methylene chloride (7.5 cc). After a reaction time of 24 hours, oct-6-en-2-one (0.044 g), the characteristics of which are identical to those of the product obtained in Example 4, is obtained with a yield of 35%.

EXAMPLE 12

The conditions of Example 10 are followed, but the starting materials are 3,4-dimethylhexa-1,5-dien-3-ol (0.126 g, 10$^{-3}$ mol), lithium trifluoromethanesulphonate (0.160 g, 10$^{-3}$ mol) and mercuric trifluoroacetate (0.100 g, 0.23.10$^{-3}$ mol) in methylene chloride (10 cc). After a reaction time of 3 hours, oct-6-en-2-one (0.065 g), the characteristics of which are identical to those of the product described in Example 11, is obtained with a yield of 52%.

EXAMPLE 13

A mixture of 4-isopropenyl-3,7-dimethylocta-1,6-dien-3-ol (0.195 g, 10$^{-3}$ mol), lithium trifluoroacetate (0.121 g) and mercuric trifluoroacetate (0.091 g) in methylene chloride (10 cc) is kept at a temperature of the order of 40° C. for 60 hours. Sodium borohydride (0.002 g) in 3 N sodium hydroxide solution (0.1 cc) is then added. The reaction mixture is extracted with methylene chloride (3×10 cc). The organic extracts are dried over magnesium sulphate. After filtration and concentration to dryness under reduced pressure (20 mm Hg; 2.7 kPa), 6,10-dimethylundeca-6,9-dien-2-one (0.078 g), the characteristics of which are identical to those of the product of Example 7, is obtained with a yield of 40%.

EXAMPLE 14

A mixture of 4-isopropenyl-3,7-dimethylocta-1,6-dien-3-ol (0.097 g, 5.10$^{-4}$ mol), lithium trifluoromethanesulphonate (0.080 ) and mercuric trifluoroacetate (0.044 g) in methylene chloride (10 cc) is kept at a temperature of the order of 20° C. for 50 minutes. A solution of sodium borohydride (0.001 g) in 3 N sodium hydroxide solution (0.05 cc) is then added. The reaction mixture is extracted with methylene chloride (3×10 cc). The organic extracts are dried over magnesium sulphate. After filtration and concentration to dryness under reduced pressure (20 mm Hg; 2.7 kPa), 6,10-dimethylundeca-6,9-dien-2-one (0.058 g), the characteristics of which are identical to those of the product of Example 7, is obtained with a yield of 60%.

EXAMPLE 15

A mixture of 1,2-divinylcyclododecan-1-ol (0.125 g, 5.10$^{-4}$ mol), lithium trifluoromethanesulphonate (0.080 g) and mercuric trifluoroacetate (0.045 g) in methylene chloride (5 cc) is kept at a temperature of the order of 20° C. for 20 minutes. The reaction mixture is washed with a saturated aqueous solution of sodium bicarbonate (3×10 cc) and then extracted with methylene chloride (3×10 cc). The organic extracts are dried over magnesium sulphate. After filtration and concentration to dryness under reduced pressure (20 mm Hg; 2.7 kPa), cyclohexadec-5-en-1-one (0.085 g) is obtained with a yield of 69%.

We claim:

1. A process for the preparation of δ-ethylenic carbonyl compounds of the general formula

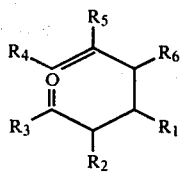

in which $R_1$, $R_2$, $R_4$, $R_5$ and $R_6$, which are identical or different, represent hydrogen or an acyclic hydrocarbon radical containing 1 to 20 carbon atoms, the chain of which may contain one or more double or triple bonds, and $R_3$ represents an acyclic hydrocarbon radical containing 1 to 20 carbon atoms, the chain of which may contain one or more double or triple bonds, it being understood that $R_1$ and $R_3$ can together form a trimethylene radical, or alternatively that $R_3$ and $R_4$ can together represent an alkylene radical $—(CH_2)_n—$, in which one or more carbon atoms may be substituted by one or more alkyl radicals containing 1 to 4 carbon atoms, and in which n represents an integer from 3 through 20 inclusive, by the rearrangement of a diethylenic alcohol of the general formula:

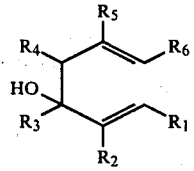

in which $R_1$, $R_2$, $R_3$, $R_4$, $R_5$ and $R_6$ are defined as above, which comprises carrying out the rearrangement at a temperature from −40° C. to 80° C., in the presence of a substantially stoichiometric amount of a mercuric salt, selected from the chloride, the acetate and the trifluoroacetate, or in the presence of a catalytic amount of a mercuric salt and a substantially stoichiometric amount of a lithium salt, and isolating the product obtained, if necessary after the reaction mixture has been treated with, as reducing agent, an alkali metal borohydride in a basic medium.

2. A process according to claim 1, wherein the rearrangement is carried out at a temperature from −5° to 30° C.

3. A process according to claim 1, wherein the reaction is carried out with a catalytic amount of mercuric salt, in the presence of a stoichiometric amount of a lithium salt selected from the trifluoroacetate and the trifluoromethanesulphonate.

4. A process according to claim 3, wherein the mercuric salt is the trifluoroacetate.

5. A process according to claim 3, wherein the mercuric salt is used in an amount of 0.01 to 0.3 mol per mol of diethylenic alcohol used.

6. A process according to claim 1 in which the alkali metal borohydride is sodium borohydride.

7. A process according to claim 1, wherein, if a catalytic amount of a mercuric salt and a substantially stoichiometric amount of a lithium salt are used, the product obtained is isolated after the reaction mixture has been treated with a basic aqueous solution.

8. A process according to claim 1, wherein a diethylenic alcohol of the general formula:

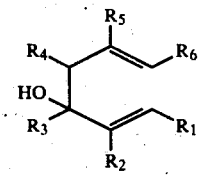

is used in which $R_2$ and $R_6$ represent a hydrogen atom, $R_1$ and $R_5$ represent a hydrogen atom or an alkyl radical containing 1 to 4 carbon atoms, $R_3$ represents an alkyl radical containing 1 to 4 carbon atoms and $R_4$ represents a hydrogen atom, an alkyl radical containing 1 to 4 carbon atoms or an alkenyl radical containing 2 to 5 carbon atoms, or alternatively $R_1$ and $R_3$ together represent a trimethylene radical, the symbols $R_2$, $R_4$, $R_5$ and $R_6$ being defined as above, or alternatively $R_3$ and $R_4$ together represent an alkylene radical $—(CH_2)_n—$ in which n is from 3 through 12 inclusive, the symbols $R_1$, $R_2$, $R_5$ and $R_6$ being defined as above.

* * * * *

UNITED STATES PATENT AND TRADEMARK OFFICE
CERTIFICATE OF CORRECTION

PATENT NO. : 4,421,934
DATED : December 20, 1983
INVENTOR(S) : Norbert BLUTHE et al It is certified that error appears in the above-identified patent and that said Letters Patent is hereby corrected as shown below:

On the title page,
In section [30] Foreign Application Priority Data, please change "01 12300" to -- 81 12300 --.

Signed and Sealed this

Fifteenth Day of October 1985

[SEAL]

Attest:

DONALD J. QUIGG

Attesting Officer

Commissioner of Patents and
Trademarks—Designate